United States Patent [19]
Chaiko

[11] Patent Number: 5,395,532
[45] Date of Patent: Mar. 7, 1995

[54] METHOD FOR EXTRACTING METALS FROM AQUEOUS WASTE STREAMS FOR LONG TERM STORAGE

[75] Inventor: David J. Chaiko, Woodridge, Ill.

[73] Assignee: The United States of America as represented by the United States Department of Energy, Washington, D.C.

[21] Appl. No.: 98,920

[22] Filed: Jul. 29, 1993

[51] Int. Cl.$^6$ .............................................. B01D 11/04
[52] U.S. Cl. .................................... 210/638; 210/639
[58] Field of Search ............... 210/634, 638, 639, 643; 423/10

[56] References Cited

U.S. PATENT DOCUMENTS 4,548,790 10/1985 Horwitz et al. .
4,574,072 3/1986 Horwitz et al. .
5,269,975 12/1993 Noakes ................................ 252/628

OTHER PUBLICATIONS

D. J. Chaiko, "Partitioning of Polymeric Plutonium (IV) in Winsor II Microemulsion Systems", Separation Science and Technology, 27(11), pp. 1389–1405, 1992.

*Primary Examiner*—Frank Spear
*Attorney, Agent, or Firm*—Bradley W. Smith; Hugh W. Glenn; William R. Moser

[57] ABSTRACT

A liquid—liquid extraction method for removing metals and hydrous metal colloids from waste streams is provided wherein said waste streams are contacted with a solvent system containing a water-in-oil microemulsion wherein the inverted micelles contain the extracted metal. A silicon alkoxide, either alone or in combination with other metal alkoxide compounds is added to the water-in-oil microemulsion, thereby allowing encapsulation of the extracted metal within a silicon oxide network. Lastly, the now-encapsulated metal is precipitated from the water-in-oil microemulsion phase to yield aggregates of metal-silicate particles having average individual particle sizes of approximately 40 nanometers.

20 Claims, 2 Drawing Sheets

METHOD FOR EXTRACTING METALS FROM AQUEOUS WASTE STREAMS FOR LONG TERM STORAGE

CONTRACTUAL ORIGIN OF THE INVENTION

The United States Government has rights in this invention pursuant to Contract Number W-31-109-ENG-38 between the United States Government and the University of Chicago representing Argonne National Laboratory.

BACKGROUND OF THE INVENTION

1. Field of the Invention

The present invention relates to a method for extracting metals from aqueous waste streams, and specifically to a method for extracting and encapsulating radioactive and toxic metals from aqueous waste streams to form monolithic structures suitable for long term storage.

2. Background Information

The hydrolysis and polymerization of metal ions, such as plutonium (IV), can cause serious problems during the aqueous processing of spent fuel and nuclear wastes. These hydrous metal polymers are resistant to extraction by ion exchange and liquid/liquid extraction systems, with emulsification and interfacial crud formation during solvent extraction remaining a major roadblock. Such polymers, such as the polymeric Pu (IV) species, exhibit a marked resistance toward depolymerization, which increases with aging at high temperatures or for extended periods of time at room temperature. This aging process involves the replacement of hydroxy bridges between the metal atoms by oxo bridges. Generally, the polymer carries a net positive charge and is readily adsorbed onto a wide variety of surfaces.

Tetravalent ions, such as Zr, Hf, Ce, Th, and U, also form polymeric species. Unlike some other polymeric metal species, however, the U and Pu species are not in equilibrium with low molecular weight intermediates. The hydrolysis of these unstable moieties leads to very rapid polymerization, producing particles of colloidal dimensions that appear not to be in equilibrium with each other or with the monomeric species. Thus, reversing the metal polymerization has not, heretofore, been a feasible process approach to extraction of these species.

The partitioning of polymeric Pu (IV) in liquid/liquid extraction systems has had very limited success. Only negligible extractability of the polymer has been achieved, using dibutylcarbitol, trifluorothiophenoxyl acetone and tributyl phosphate (TBP). Each of the solvents is effective at monomeric Pu (IV) extraction. Previous methods (U.S. Pat. Nos. 4,548,790 and 4,574,072) to extract actinides and lanthanides from aqueous waste streams have utilized bidentate organophosphorus extractants in combination with normal paraffinic hydrocarbon diluents.

The undesirable formation of interfacial crud is a problem associated with all of the above-identified extraction systems, as the crud interferes with interfacial mass transfer of the metals being extracted.

No solvent extraction systems have been shown to successfully extract hydrous metal polymers, such as polymeric Pu(IV), giving 100 percent bulk liquid phase recovery.

There is a need for an economical and compact method to extract and encapsulate hydrous metal polymers and unhydrolyzed metal ions from aqueous solutions which are often part of specialized waste streams containing radioactive and RECRA metals. This need also extends to the treatment of secondary waste streams generated from environmental remediation and waste management activities. Such a system would provide the capability to extract and encapsulate metals whereby hazardous materials are removed from aqueous waste streams and recovered directly from an organic solvent in a single step. These hazardous metals should then be easily treated to produce stable bulk materials for safe storage by exhibiting superior resistance to physical or chemical degradation.

SUMMARY OF THE INVENTION

It is an object of the present invention to provide a method for extracting metal ions, hydrolyzed metal ions, and hydrous metal polymers from a waste stream which overcomes many of the disadvantages of the prior art.

It is another object of the present invention to provide a method to encapsulate actinide and lanthanide materials. A feature of the invention is the extraction of metal ions, hydrolyzed metal ions, hydrous metal polymers and combinations thereof from aqueous solutions. An advantage of the invention is to facilitate the formation of a ceramic monolith in which actinide and lanthanide-containing particles are homogeneously distributed.

Yet another object of the present invention is to provide a method of extracting radioactive and/or toxic metals from aqueous waste streams. A feature of the present invention is the utilization of a microemulsion-based solvent system. An advantage of the invention is the attainment of extremely high partition coefficients, with a concomitant decrease in the formation of interfacial crud and a third phase.

Still another object of the present invention is to provide an economical method to formulate and extract extremely small hydrous metal particles from an aqueous waste stream. A feature of the present method is the separation and encapsulation of aqueous metal species carried out at room temperatures and pressures. An advantage of the invention is a significant reduction in treatment costs viz-a-viz more conventional glass encapsulation scenarios wherein processing temperatures in excess of 1,100° C. are required.

Another object of the present invention is to increase the recovery yield for hydrous metal species from aqueous solutions. A feature of the invention is the utilization of microemulsion-based solvent extraction systems formed by mixing metal extractants with surfactants and silicon compounds. An advantage of the invention is the attainment of bulk phase mass balances of 100 percent for certain metals.

Yet another object of the present invention is to provide a method to extract and encapsulate a wide range of radioactive elements or heavy metals from primary or secondary aqueous waste streams. A feature of this invention is the exclusion of the formation of macroemulsions. An advantage of this invention is the formation of extremely small silica-based particles, which can facilitate the production of very dense monolith storage structures.

Briefly, the invention provides for a method for extracting a metal material from a waste stream comprising mixing the waste stream with an organic fluid consisting of a metal extractant, a surfactant and an organic diluent in predetermined proportions to provide a water-in-oil microemulsion, solubilizing the metal material within the inverted micelles, mixing a hydrolyzable alkoxy compound containing silicon with the solubilized metal to form metal-silicate particles, adding a sufficient amount of an alkaline material so as to precipitate the metal-silicate particles from the organic phase, drying the precipitate, and sintering the precipitate at a predetermined temperature and for a predetermined time so as to produce a monolithic structure, or, instead of sintering the precipitate, chemically bonding the precipitate with phosphate binders to form a resilient aggregate.

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
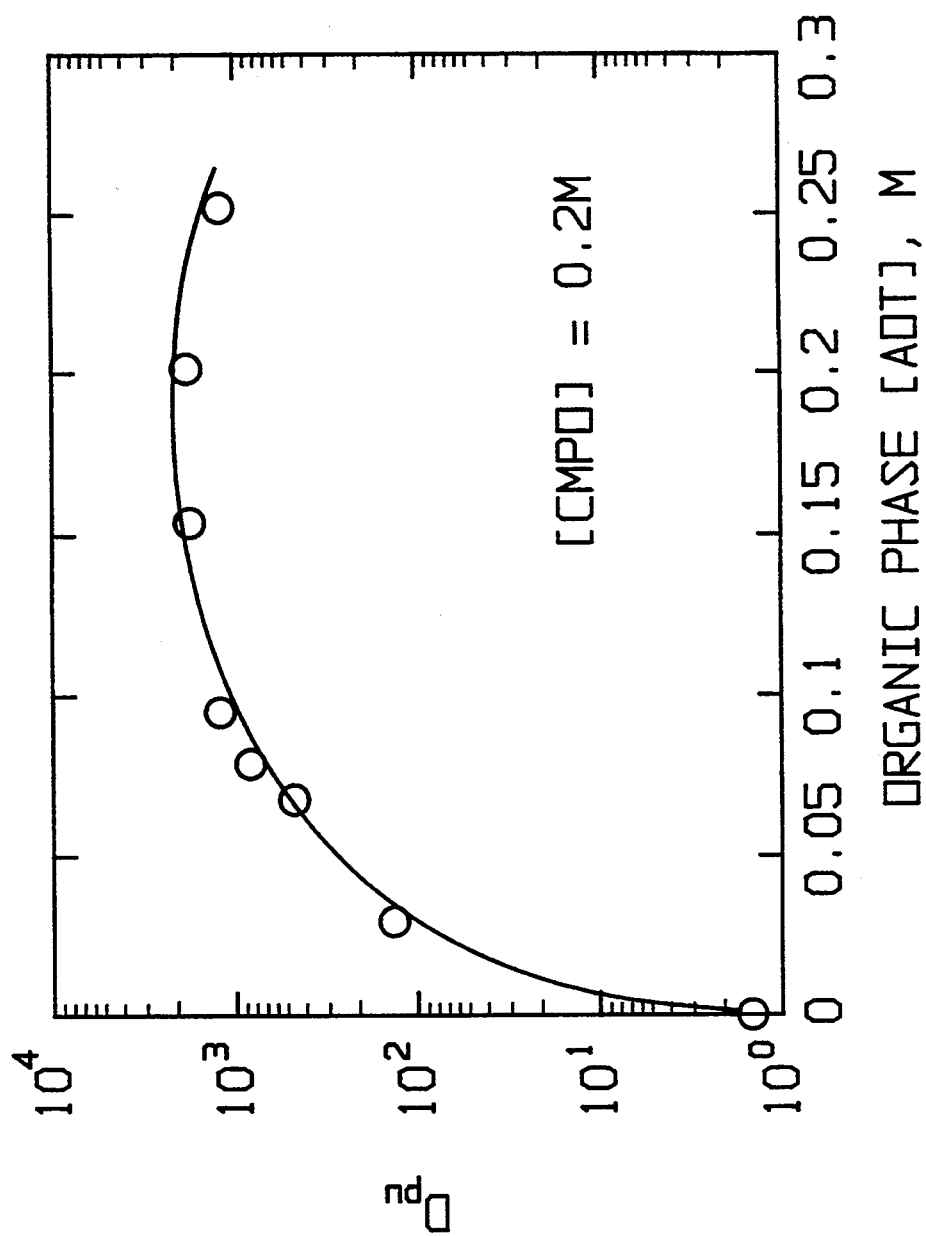
FIG. 1 is a graph depicting the partition coefficient values of polymeric plutonium from acidic solutions as a function of organic phase surfactant concentration, illustrating the present invention.

Advanced microemulsion-based solvent extraction systems for extraction and encapsulation of metals from both acid and basic waste streams have been developed. Advanced surfactant/extraction combinations are employed to permit radionuclide extraction from a variety of aqueous feeds. The method allows for extraction of individual radioisotopes alone and in combination with complex waste mixtures containing other actinides and/or lanthanides. The method is also applicable to extract heavy metals, such as lead, mercury, zinc, and other metals found in waste streams associated with electroplating and electropolishing operations.

This novel method effects back-extraction of metals from loaded water-in-oil microemulsions that contain monofunctional extractants, such as tri-n-butyl phosphate and hydroxy oximes, and bifunctional extractants, such as n-octyl(phenyl)N,N-diisobutylcarbamoylmethylphosphine oxide (CMPO). Such a microemulsion system, when in equilibrium with a high ionic strength aqueous phase, are known as Winsor Type II microemulsions.

During the extraction process, hydrated metal ions are transferred from the aqueous feed to the aqueous core of the reverse micelles located in the organic phase. Back-extraction from the microemulsion phase is achieved by a novel technique that involves the encapsulation of the extracted metal species within nanometer-scale $SiO_2$ matrices. The silica capsules are produced by a sol-gel technique that utilizes the aqueous microdroplets of the organic phase as a type of microscale chemical reactor.

The leach resistant capsules are harvested from the microemulsion by a pH dependent agglomeration process. Once harvested, the metal-silica particles can be chemically treated to produce an ultra-dense, ceramic-based waste form that is extremely leach resistant.

Formation of Metal-$SiO_2$ Particles

After extraction of the metal species from the aqueous phase and into the aqueous cores of the inverted micelles, a silicon alkoxide is added to the reaction liquor to create a $SiO_2$ network in a molar ratio of alkoxide to aqueous metal species of between approximately 10:1 to 100:1.

The $SiO_2$ network is generated within the aqueous microdroplets of the microemulsion by the hydrolysis of metal alkoxides such as tetraethoxysilane (TEOS), tetramethylorthosilicate individually or in combination with transition metal alkoxides, such as titanium alkoxide, vanadium alkoxide or zirconium alkoxide. The silicon alkoxides are readily available for many chemical suppliers, such as Aldrich.

Attachment of the extracted plutonium species to the micro-scale silica particles occurs via a condensation reaction between the hydroxyl groups in the growing silica particle and a hydrolyzed metal ion, or through ion exchange of an unhydrolyzed metal cation with silanol protons. This attachment phenomenon is simplified in Equation 1, below:

$$Si—OR+HO—M \rightarrow Si—O—M+ROH \qquad (1)$$

Metal-laden silica particles generated by this process typically exhibit ultra fine diameters, i.e., diameters below one micron (1 μm), and more typically exhibit diameters in the nanometer (nm) range. Transmission electron microscopy and dynamic laser light scattering data has determined that the particles produced in this method range in size from 10 nm to 100 nm with an average size of about 40 nm, which corresponds in size to that of the micelle core.

After interaction of the metal with the silica particles within the microscopic reaction vessels embodied by the inverted micelles, back extraction is performed on the emulsion system. Upon increasing the pH of the aqueous micelle core (above pH2-3), the silicon takes on a negative surface charge at the same time that the surfactant deprotonates. Charge repulsion from the aqueous core of the anionic AOT micelles occurs, resulting in the silica particles being rejected from the micelle cores and precipitated from the organic phase. The metal-silica interaction is not adsorptive, but rather covalent, as evidenced by the fact that simply adding externally formed colloidal silica particles to the loaded organic phase, in the place of TEOS, produced no noticeable reduction in the organic phase plutonium concentration when the colloidal silica was subsequently precipitated by addition of either $N_2H_4$ or $NH_4OH$. In addition, that Pu-containing $SiO_2$ particles are solubilized within the micelle core in acidic conditions is supported by observing no change in mass balance upon removal of macroscale silica particles from the reaction liquor. When these macroscale silica particles, formed by the hydrolysis and polymerization reactions taking place outside of the aqueous micelle cores, are removed by centrifuging without first raising the pH, no detectable change in organic phase plutonium concentration is noted.

The rate of formation of the silica particles depends on the concentration of certain catalysts in the aqueous micelle phase. A myriad of catalysts contained in the aqueous phase effect the rate of particle formation, including, but not limited to $HNO_3$, $H_2SO_4$, HF, and HCl. Other catalysts used to enhance the kinetics of the condensation include, but are not limited to, titanium alkoxides and vanadium alkoxides. Furthermore, under the robust reaction conditions used, (i.e., excess TEOS concentrations) two different types of $SiO_2$ particles are produced: (a) macro-scale silica particles, which are produced from the very rapid hydrolysis of TEOS and are easily recovered by centrifugation, and (b) microscale silica particles, which are responsible for the encapsulation of the extracted plutonium polymer and remain solubilized within the reversed micelles. These microscale particles cannot be recovered by centrifugation unless a base, such as $NH_4OH$, hydrazine, and/or others discussed infra, is used to eject the particles from the micelle core, thereby leading to coagulation and flocculation.

Reaction Conditions Detail

An advantage of this invented method is that the above referenced reaction mechanism to extract metal from an aqueous stream and embed said metal in a silica matrix can be carried out at normal atmospheric pressures and temperatures, compared to the more stringent operating parameters of typical encapsulation processes wherein the melting of glass is an integral part. For example, while such glass melting processes require temperatures of approximately 1,200° C., the invented process requires temperatures selected from the range of approximately 10° C. and 70° C., and more preferably from between approximately 20° C. and 30° C., i.e., room temperature. Generally, to avoid phase changes in any of the solutions, temperatures are selected between the temperatures that those solutions may freeze or boil.

The invented method allows for the attainment of extremely high separation values. As can be noted in FIG. 1, the partition coefficients, or distribution coefficients, for the separation of polymeric Pu (IV) reach 1000, which is three orders of magnitude higher than those attained from previous solvent extraction systems employed.

Aside from plutonium, the invented method is also applicable to attain high partition coefficients for other similar metals, such as zirconium, hafnium, cerium, thorium, americium, tungsten and uranium.

Solvent Detail

As noted, supra, the formation of the Winsor Type II microemulsion system requires establishing an organic phase. A bifunctional solvent extractant having the general structural formula:

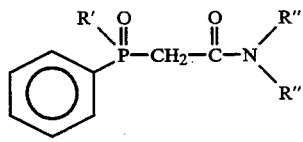

where R' is a straight or branched alkyl or alkoxyalkyl containing from six to 12 carbon atoms, and R" is a straight or branched alkyl containing from 3 to 6 carbon atoms, comprises the bulk of the solvent phase. One such molecule, octylphenyl-N,N-diethyl carbamoylmethyl phosphonate (CMPO), and a myriad of solvents utilized as organic phase diluents, comprises the organic phase of this emulsion system. Such diluents include, but are not limited to, hexane, dodecane and generally those compounds with low vapor pressures, relative to that of hexane. Solvents ranging in chain length from approximately six carbons to 12 carbons are good solvent-diluent candidates.

Solvents containing the surfactant AOT, discussed infra, often produce macroemulsions with n-alkyl diluents with chain lengths above $C_8$-$C_{10}$. To prevent the formation of such macroemulsions, extractions can be carried out in a supported membrane extractor. Another advantage to using a supported membrane extractor is the extremely low level of other-phase carry over and back-mixing that is attainable with this configuration. Thus, organic contamination of the aqueous raffinate stream is avoided while very large partition coefficients are attained during continuous, counter-current extraction.

Surfactant Detail

One of the novel features of the invented method is combining a metal extractant with a surfactant to form mixed micelles. Choice of surfactant is crucial. For example, the surfactant sodium bis(2-ethyl-hexyl)sulfosuccinate, (AOT), surprisingly and unexpectedly was found by the inventor to completely inhibit adsorption of polymeric plutonium onto solid surfaces. The combination of this surfactant interacting with many of the hydrous metals of interest and the more typical surfactant characteristic of absorbing at the solvent-water interface makes AOT a particularly good choice in forming a monolayer film to effect the inverted micelles to contain polymeric Pu(IV), monomeric Pu(IV), Am (111), and other similar metals from the actinide and lanthanide series. Other polymeric metals, such as zirconium, thorium, uranium, hafnium, cerium and tungsten could also be extraction candidates with the CMPO/AOT microemulsion system. This system is also applicable to the extraction of iron. Iron, and other common metals, such as copper and nickel would be extracted using a different surfactant, such as dinonylnaphthalene sulfonic acid and a different metal extractant, such as a hydroxy oxime, as CMPO does not extract Ni and Cu by itself.

The inventor has found that microemulsions formed by the combining of AOT and CMPO is particularly effective in metal extraction and stripping, due to specific interactions between AOT and CMPO which lead to incorporation of CMPO into AOT micelles, thus forming a mixed micelle. Data of such extractions are depicted in FIG. 1, wherein metal is extracted from 1M $HNO_3$ solutions with CMPO concentrations held constant at 0.2M, the variable factor being AOT concentration. Because of a tendency toward macroemulsion formation with aqueous phases of low ionic strengths, n-hexane was used as the diluent in place of n-dodecane.

Figure 2:
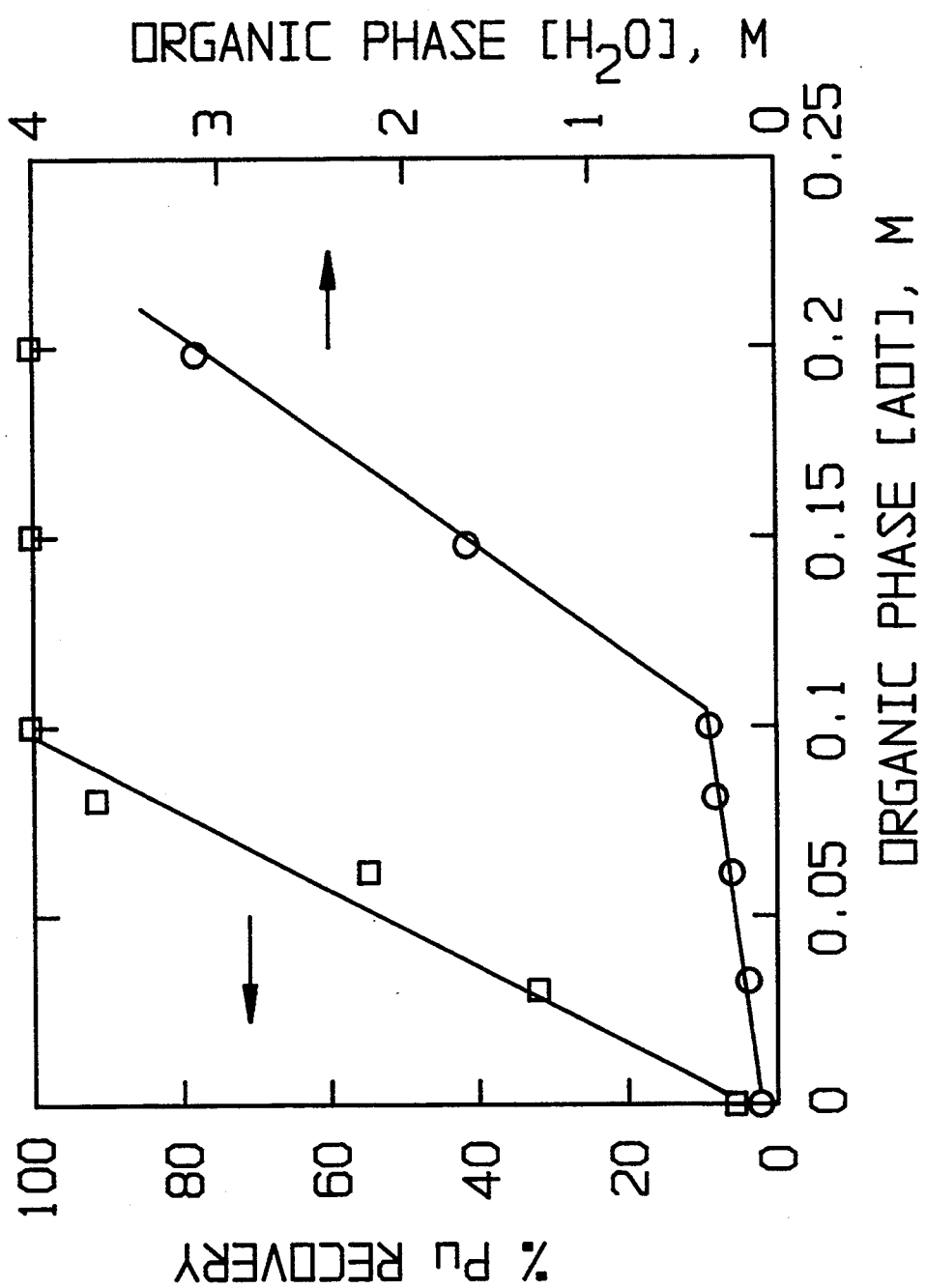
FIG. 2 is a graph depicting bulk phase recovery values for polymeric plutonium (IV), illustrating the present invention.

As the AOT concentration in CMPO/AOT mixtures increased, the plutonium partition coefficient values ($D_{Pu}$)values increased dramatically and became substantially larger than those obtained with either CMPO or AOT alone. A maximum $D_{Pu}$ was obtained at a CMPO:AOT molar ratio of one, as illustrated in FIG. 1. CMPO/AOT systems also exhibited extremely good bulk phase recovery ($R_{Pu}$) values of polymeric Pu(IV). As depicted in FIG. 2, a linear increase in $R_{Pu}$ occurred as the ratio of [AOT]/[OMPO] increased from 0 to 0.5, with 100 percent recovery occurring at 0.1M AOT. The data points depicted in FIG. 2 were derived with a constant CMPO concentration of 0.2M, so that at 0.1M AOT, the [AOT]/[CMPO] ratio was 0.5. Generally, metal extractant to surfactant ratios range from between approximately 1:0.5 to 1:2. Polymer extraction increased rapidly with increasing $HNO_3$ concentration until a maximum in $D_{Pu}$ of 3000 is reached at 0.4M $HNO_3$.

Mixtures of TBP and AOT in hexane also promoted enhanced polymeric Pu(IV) extraction from aqueous $HNO_3$ solutions, with $D_{Pu}$ values of 200 being attained. Plutonium recoveries of 100 percent were also attained. A lower partition coefficient for the TBP/AOT system is indicative of relatively little interaction occurring between the TBP and the micelle viz. CMPO-micelle interaction

Alkaline Agent Detail

Expulsion of the silicate particles from the inverted micelles occurs as the pH of the emulsion is increased. A myriad of bases can be used to increase the pH, including, but not limited to, hydrazine, NaOH, KOH, $NH_4OH$, and combinations thereof with $NH_4OH$ and hydrazine providing superior results. The inventor has found that the water associated with the sodium and potassium systems contributes to the formation of a liquid-liquid phase separation and therefore destabilizes the microemulsion liquor.

Experimental Procedure

Small angle neutron scattering (SANS) of polymeric Pu(IV) in aqueous solutions depicts the polymer as an elongated particle having a diameter of $22+3\text{Å}$ and a length of $120+10\text{Å}$. The x-ray diffraction lines agreed with those of crystalline $PuO_2$, indicating a crystal structure that is of the fluorite-type with eight oxygen atoms surrounding each plutonium atom.

Distribution ratios of polymeric Pu(IV) between aqueous $HNO_3$ solutions and organic solvents containing either CMPO, tributyl phosphate (TBP) (also available from Aldrich) or CMPO/AOT, TBP/AOT mixtures were measured at an aqueous/organic phase ratio of one and a total liquid volume of either 1 or 2 milliliters (ml). All equilibrations were carried out at 25° C. using a thermostated water bath. With the exception of the TBP/AOT system, extraction equilibrium was reached after one minute of contact using a vortex mixer. The phases were separated by centrifugation for a period of 10 minutes to produce two clear phases. For the TBP/AOT systems, the two phases were vortexed for one minute and then placed in a thermostated water bath at 25° C. where the two phases were allowed to remain in contact overnight (>12 hours). All $^{239}$Pu distribution ratios ($D_{Pu}$) were determined by measuring the alpha activity in appropriate aliquot sizes from each phase with a liquid scintillation counter (Packard Tri-Carb). Extraction equilibrium was considered to have been reached when the Pu distribution ratios were the same regardless of whether the Pu polymer was added first to the organic phase or to the aqueous phase. Organic phase water concentrations were measured by Karl Fischer titration using a Metrohm 652 KF-Coulometer. The organic phase hydrogen ion concentrations were measured by direct titration of organic phase aliquots with standardized isopropanol solutions of tetrabutylammonium hydroxide. Plutonium partitioning between bulk aqueous and organic phases and the liquid/liquid interface was measured using the following procedure: The organic and aqueous phases were equilibrated, and portions of the top and bottom phases were removed and placed in separate vials for sampling. The remaining interphase region and bulk phase samples were then recombined, and a sufficient volume of a 1:1, acetone:Triton X-100 solution was added to produce a homogenous, optically transparent emulsion. The amount of Pu adsorbed at the liquid/liquid interface was determined from a mass balance of the alpha activity present in the individual bulk phases and the recombined-emulsified sample. The amount of Pu adsorbed at the liquid/solid interface in the test tube was determined from a mass balance of the alpha activity originally put into the system and the amount recovered from the bulk phases and the liquid/liquid interface.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for extracting a metal material from a waste stream comprising:
   a.) mixing the waste stream with an organic fluid consisting of a metal extractant, a surfactant and an organic diluent in predetermined proportions so as to form an organic phase and an inorganic phase;
   b.) allowing a microemulsion containing inverted micelles to form in the organic phase;
   c.) solubilizing the metal material within the inverted micelles;
   d.) mixing a hydrolyzable alkoxy compound containing silicon with the solubilized metal to form metal-silicate particles;
   e.) adding a sufficient amount of an alkaline material so as to precipitate the metal silicate particles from the organic phase;
   f.) drying the precipitate at a predetermined temperature and for a predetermined time; and
   g.) sintering the precipitate at a predetermined temperature so as to produce a monolithic structure.

2. The method as recited in claim 1 wherein the predetermined proportions of the metal extractant and the surfactant range from approximately 1:0.5 to 1:2 molar.

3. The method as recited in claim 1 wherein the metal material is selected from the group consisting of a hydrous metal polymer, metal ion, hydrolyzed metal ion, and combinations thereof.

4. The method as recited in claim 1 wherein the metal material is selected from the group consisting of polymeric plutonium(IV), zirconium, hafnium, iron, an actinide element, a lanthanide element, and combinations thereof.

5. The method as recited in claim 1 wherein the metal extractant has the following formula:

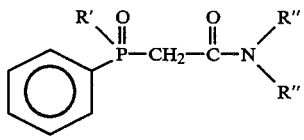

where R' is a straight or branched alkyl or alkoxyalkyl containing from six to 12 carbon atoms, and R" is a straight or branched alkyl containing from 3 to 6 carbon atoms.

6. The method as recited in claim 1 wherein the metal extractant is selected from the group consisting of octylphenyl-N,N-diisobutylcarbamoylmethylphosphine oxide, tributyl phosphate, hydroxy oximes, and combinations thereof.

7. The method as recited in claim 1 wherein the organic diluent is a straight chain carbon compound having a chain length of between approximately six and 12 carbons.

8. The method as recited in claim 1 wherein the surfactant is selected from the group consisting of sodium bis(2-ethylhexyl) sulfosuccinate, dinonylnaphthalene sulfonic acid, and combinations thereof.

9. The method as recited in claim 1 wherein the hydrolyzable alkoxy compound containing silicon is a silicon alkoxide compound alone or in combination with an alkoxide containing a metal selected from the group consisting of vanadium, zirconium, titanium and combinations thereof.

10. The method as recited in claim 1 wherein the alkaline material is selected from the group consisting of hydrazine, ammonium hydroxide, potassium hydroxide, sodium hydroxide and combinations thereof.

11. The method as recited in claim 1 wherein the steps of mixing the waste stream with an organic fluid, a surfactant and an organic diluent in predetermined proportions so as to form an organic phase and an inorganic phase, allowing a microemulsion containing inverted micelles to form in the organic phase, solubilizing the metal material within the inverted micelles, mixing an alkoxide compound containing silicon with the solubilized metal to form metal silicate particles, and adding a sufficient amount of an alkaline material so as to precipitate the metal silicate particles from the organic phase occur at a temperature selected from a range of between approximately 10° C. and 70° C.

12. The method as recited in claim 1 wherein the second predetermined temperature is selected from a range of between approximately 400° C. and 900° C.

13. The method as recited in claim 1 wherein the step of adding a sufficient amount of an alkaline material further consists of raising the pH of the organic phase and the inorganic phase to at least approximately 2.

14. The method as recited in claim 1 wherein the hydrolyzable alkoxide compound containing silicon is mixed with the solubilized aqueous metal species in a silicon:metal molar ratio selected from a range of between approximately 10:1 to 100:1.

15. A method for extracting radioactive metals from an aqueous solution comprising:
a.) mixing the waste stream with dodecane and octylphenyl-N,N-diisobutylcarbamoylmethylphosphine oxide and sodium bis(2-ethylhexyl) sulfosuccinate so as to form an organic phase and an inorganic phase;
b.) allowing a microemulsion containing inverted micelles to form in the organic phase;
c.) solubilizing the radioactive metals within the inverted micelles;
d.) mixing a silicon alkoxide with the solubilized radioactive metals to form metal silicate particles;
e.) adding a sufficient amount of NH$_4$OH so as to precipitate the radioactive, metal silicate particles from the organic phase;
f.) drying the precipitate at a predetermined temperature; and
g.) sintering the precipitate at a predetermined temperature so as to produce a monolithic structure.

16. The method as recited in claim 15 wherein the octylphenyl-N,N-diisobutylcarbamoylmethylphosphine oxide and sodium bis(2-ethylhexyl) sulfosuccinate are combined in a molar ratio selected from a range of between approximately 1:0.5 and 1:2.

17. The method as recited in claim 15 wherein the steps of mixing the waste stream with dodecane and octylphenyl-N,N-diisobutylcarbamoylmethylphosphine oxide and sodium bis(2-ethylhexyl) sulfosuccinate in predetermined proportions so as to form an organic phase and an inorganic phase, allowing a microemulsion containing inverted micelles to form in the organic phase, solubilizing the radioactive metals within the inverted micelles, mixing a silicon alkoxide with the solubilized radioactive metals to form metal silicate particles, and adding a sufficient amount of NH$_4$OH so as to precipitate the radioactive metal silicate particles from the organic phase occur at a temperature selected from a range of between approximately 10° C. and 70° C.

18. The method as recited in claim 15 wherein the predetermined sintering temperature is selected from a range of between approximately 400° C. and 900° C.

19. The method as recited in claim 15 wherein the radioactive metals are selected from the group consisting of polymeric Plutonium (IV), monomeric Pu (IV), monomeric Am (III) and combinations thereof.

20. A method for extracting polymeric Plutonium (IV) from an aqueous solution comprising:
a.) mixing the aqueous solution with dodecane and a 2:1 molar ratio mixture of octylphenyl-N,N-diisobutylcarbamoylmethylphosphine oxide and sodium bis(2-ethylhexyl) sulfosuccinate so as to form an organic phase and an inorganic phase;
b.) allowing a microemulsion containing inverted micelles to form in the organic phase;
c.) solubilizing the polymeric Plutonium (IV) within the inverted micelles;
d.) mixing hydrolyzed tetraethoxysilane with the solubilized metal to form metal silicate particles having an average particle diameter of approximately 40 nm;
e.) adding a sufficient amount of NH$_4$OH so as to precipitate the Plutonium (IV) silicate particles from the organic phase;
f.) drying the precipitate at approximately 100° C.; and
g.) sintering the precipitate at between 400° C. and 900° C.

* * * * *